(12) United States Patent
O'Donnell et al.

(10) Patent No.: US 12,121,661 B2
(45) Date of Patent: Oct. 22, 2024

(54) PRESSURIZING MASKS, SYSTEMS AND METHODS

(71) Applicant: Fisher & Paykel Healthcare Limited, Auckland (NZ)

(72) Inventors: Kevin Peter O'Donnell, Auckland (NZ); Robert Stuart Kirton, Auckland (NZ); Sean Joel Babbage, Auckland (NZ); Dean Antony Barker, Auckland (NZ); Stanislav Tatkov, Auckland (NZ)

(73) Assignee: FISHER & PAYKEL HEALTHCARE LIMITED, Auckland (NZ)

( * ) Notice: Subject to any disclaimer, the term of this patent is extended or adjusted under 35 U.S.C. 154(b) by 0 days.

(21) Appl. No.: 17/451,239

(22) Filed: Oct. 18, 2021

(65) Prior Publication Data

US 2022/0096772 A1     Mar. 31, 2022

Related U.S. Application Data

(63) Continuation of application No. 15/128,906, filed as application No. PCT/IB2015/052257 on Mar. 27, 2015, now Pat. No. 11,185,653.

(Continued)

(51) Int. Cl.
*A61M 16/06* (2006.01)
*A61M 16/20* (2006.01)

(52) U.S. Cl.
CPC ........ *A61M 16/0666* (2013.01); *A61M 16/06* (2013.01); *A61M 16/0605* (2014.02);
(Continued)

(58) Field of Classification Search
CPC .............. A61M 16/0666; A61M 16/06; A61M 16/0605; A61M 16/0672; A61M 16/0683;
(Continued)

(56) References Cited

U.S. PATENT DOCUMENTS

| 1,896,716 A | 2/1933 | McKesson |
| 2,156,852 A * | 5/1939 | Horak .................... A62B 18/02 128/206.28 |

(Continued)

FOREIGN PATENT DOCUMENTS

| AU | 2010335069 | 6/2011 |
| CN | 101489617 | 7/2009 |

(Continued)

OTHER PUBLICATIONS

Australian Examination Report 1 for Patent Application No. 2010335069 dated Apr. 30, 2015, 6 pages.

(Continued)

*Primary Examiner* — Elliot S Ruddie
(74) *Attorney, Agent, or Firm* — Knobbe Martens Olson & Bear LLP

(57) ABSTRACT

A respiratory mask or other sealing interface can be used in combination with a nasal cannula or other unsealing interface in providing respiratory therapies for the treatment of COPD or OSA. The mask can act as a pressure vessel over the top of a nasal cannula, with the intention of increasing expiratory pressure whilst allowing the nasal cannula to provide a user with breathing gases of a high humidity and temperature. The ability to selectively apply increased expiratory pressure may be effective in reducing a user's breathing rate and thus beneficial in the treatment of respiratory distress.

20 Claims, 7 Drawing Sheets

Related U.S. Application Data

(60) Provisional application No. 61/971,464, filed on Mar. 27, 2014.

(52) U.S. Cl.
 CPC .... *A61M 16/0672* (2014.02); *A61M 16/0683* (2013.01); *A61M 16/208* (2013.01)

(58) Field of Classification Search
 CPC .............. A61M 16/208; A61M 16/202; A61M 16/0069; A61M 2016/0027; A62B 18/02–025; A62B 18/10; A62B 23/00–025; A41D 13/11–1192
 See application file for complete search history.

(56) References Cited

U.S. PATENT DOCUMENTS

| | | | |
|---|---|---|---|
| 2,313,999 A | | 3/1943 | Kreiselman |
| 2,341,566 A | * | 2/1944 | Monro ................... A62B 18/02 128/202.13 |
| 2,375,803 A | | 5/1945 | Chase et al. |
| 2,663,297 A | | 12/1953 | Turnberg |
| 2,675,803 A | | 4/1954 | Kaslow |
| 2,693,800 A | | 11/1954 | Caldwell |
| 2,868,199 A | | 1/1959 | Hudson |
| 3,330,274 A | | 7/1967 | Bennett |
| 3,513,844 A | | 5/1970 | Smith |
| 3,968,812 A | * | 7/1976 | Eross ................ A61M 16/0816 128/205.12 |
| 4,201,205 A | | 5/1980 | Bartholomew |
| 4,231,363 A | | 11/1980 | Grimes |
| 4,248,218 A | | 2/1981 | Fischer |
| 4,328,767 A | | 5/1982 | Peterson |
| 4,328,797 A | * | 5/1982 | Rollins, III ........... A61M 16/06 128/912 |
| 4,354,488 A | | 10/1982 | Bartos |
| 4,944,310 A | | 7/1990 | Sullivan |
| 5,005,571 A | * | 4/1991 | Dietz .................... A61M 16/06 128/207.18 |
| 5,400,781 A | | 3/1995 | Davenport |
| 5,474,060 A | | 12/1995 | Evans |
| 6,357,437 B1 | | 3/2002 | Jacques |
| 6,418,928 B1 | | 7/2002 | Bordewick et al. |
| 6,561,190 B1 | | 5/2003 | Kwok |
| 6,679,265 B2 | | 1/2004 | Strickland et al. |
| 7,255,107 B1 | | 8/2007 | Gomez |
| 7,341,059 B2 | | 3/2008 | Moody et al. |
| 7,406,966 B2 | | 8/2008 | Wondka |
| 7,493,902 B2 | | 2/2009 | White et al. |
| 7,559,327 B2 | | 7/2009 | Hernandez |
| 7,958,889 B1 | * | 6/2011 | Fernandez-Decastro ................... A41D 13/11 128/205.27 |
| 8,342,179 B2 | | 1/2013 | Hacke et al. |
| 8,844,530 B2 | | 9/2014 | Birnkrant |
| 9,032,955 B2 | | 5/2015 | Lubke et al. |
| 10,556,079 B2 | | 2/2020 | Tatkov |
| 11,185,653 B2 | | 11/2021 | O'Donnell et al. |
| 11,826,509 B2 | | 11/2023 | Nelson et al. |
| 2002/0053347 A1 | | 5/2002 | Ziaee |
| 2002/0112730 A1 | | 8/2002 | Dutkiewicz |
| 2002/0122746 A1 | | 9/2002 | Yamamori et al. |
| 2003/0024533 A1 | * | 2/2003 | Sniadach ............. A61M 16/06 128/206.28 |
| 2003/0168063 A1 | | 9/2003 | Gambone et al. |
| 2004/0244799 A1 | | 12/2004 | Landis |
| 2004/0261797 A1 | * | 12/2004 | White ............... A61M 16/0057 128/206.11 |
| 2005/0011523 A1 | | 1/2005 | Aylsworth et al. |
| 2005/0028822 A1 | | 2/2005 | Sleeper et al. |
| 2005/0066976 A1 | | 3/2005 | Wondka |
| 2005/0098183 A1 | | 5/2005 | Nash |
| 2006/0081243 A1 | | 4/2006 | McDonald et al. |
| 2006/0169281 A1 | | 8/2006 | Aylsworth et al. |
| 2006/0266361 A1 | | 11/2006 | Hernande |
| 2006/0278233 A1 | | 12/2006 | McAuley et al. |
| 2007/0079982 A1 | | 4/2007 | Laurent et al. |
| 2007/0089749 A1 | | 4/2007 | Ho et al. |
| 2007/0107737 A1 | | 5/2007 | Landis et al. |
| 2007/0113848 A1 | | 5/2007 | Acker et al. |
| 2007/0113856 A1 | | 5/2007 | Acker et al. |
| 2007/0125380 A1 | | 6/2007 | Acker et al. |
| 2007/0125385 A1 | | 6/2007 | Ho et al. |
| 2007/0144518 A1 | | 6/2007 | Acker et al. |
| 2008/0060653 A1 | | 3/2008 | Hallett et al. |
| 2008/0078389 A1 | | 4/2008 | Xiao et al. |
| 2008/0276937 A1 | | 11/2008 | Davidson et al. |
| 2008/0295846 A1 | | 12/2008 | Han et al. |
| 2008/0319334 A1 | | 12/2008 | Yamamori |
| 2009/0000618 A1 | | 1/2009 | Warren |
| 2009/0101147 A1 | | 4/2009 | Landis et al. |
| 2009/0173349 A1 | | 7/2009 | Hernandez et al. |
| 2009/0250060 A1 | * | 10/2009 | Hacke ................... A61M 16/06 128/205.12 |
| 2011/0009763 A1 | | 1/2011 | Levitzky et al. |
| 2011/0067704 A1 | | 3/2011 | Kooij et al. |
| 2012/0055480 A1 | | 3/2012 | Wilkinson |
| 2012/0125338 A1 | | 5/2012 | Yarahmadi |
| 2012/0167892 A1 | | 7/2012 | Matula |
| 2012/0240935 A1 | | 9/2012 | Johansen |
| 2012/0285448 A1 | | 11/2012 | Dugan et al. |
| 2012/0305001 A1 | | 12/2012 | Tatkov |
| 2013/0213400 A1 | | 8/2013 | Barlow et al. |
| 2014/0096773 A1 | | 4/2014 | Amarasinghe |
| 2014/0107517 A1 | | 4/2014 | Hussain |
| 2014/0166015 A1 | | 6/2014 | Waggoner |
| 2014/0246025 A1 | * | 9/2014 | Cragg ................ A61M 16/0866 128/204.19 |
| 2015/0217074 A1 | | 8/2015 | Wells |
| 2016/0022948 A1 | | 1/2016 | Martin et al. |
| 2016/0082215 A1 | | 3/2016 | Bugamelli et al. |
| 2016/0282215 A1 | | 3/2016 | Bugamelli et al. |
| 2016/0296720 A1 | | 10/2016 | Henry et al. |
| 2016/0339195 A1 | | 11/2016 | Raje et al. |
| 2017/0182275 A1 | | 1/2017 | O'Donnell et al. |
| 2017/0128689 A1 | | 5/2017 | Law et al. |
| 2017/0173291 A1 | | 6/2017 | Pedro et al. |
| 2019/0351168 A1 | | 11/2019 | Tatkov |
| 2020/0010250 A1 | | 4/2020 | Nelson et al. |
| 2020/0101250 A1 | | 4/2020 | Nelson et al. |

FOREIGN PATENT DOCUMENTS

| | | |
|---|---|---|
| CN | 202590116 | 12/2012 |
| CN | 103405843 | 11/2013 |
| EP | 0747078 | 10/2002 |
| EP | 1484075 | 12/2004 |
| EP | 1800707 | 6/2007 |
| EP | 1334742 | 4/2008 |
| EP | 2515984 A1 | 10/2012 |
| EP | 3122408 | 2/2017 |
| EP | 3556418 | 10/2019 |
| EP | 3808399 | 4/2021 |
| JP | 2009-512510 | 3/2009 |
| JP | 2013-507205 | 3/2013 |
| JP | 2013-515560 | 5/2013 |
| WO | WO 82/03548 | 10/1982 |
| WO | WO 2005/018524 | 3/2005 |
| WO | WO 2005/063328 | 7/2005 |
| WO | WO 2008/031149 | 3/2008 |
| WO | WO 2009/109005 | 9/2009 |
| WO | WO 2010/057166 | 5/2010 |
| WO | WO 2010/076704 | 7/2010 |
| WO | 2011/030250 A1 | 3/2011 |
| WO | WO 2011/078702 | 6/2011 |
| WO | WO 2011/078703 | 6/2011 |
| WO | WO 2012/154883 | 11/2012 |
| WO | WO 2015/145390 | 3/2015 |
| WO | WO 2016/041019 | 3/2016 |

(56) References Cited

FOREIGN PATENT DOCUMENTS

| WO | WO 2016/201358 | 12/2016 |
| WO | WO 2017/011864 | 1/2017 |

OTHER PUBLICATIONS

Australian Examination Report No. 1 for Standard Patent Application, Application No. 2015237807, dated Dec. 21, 2018, in 4 pages.
Chinese Patent Office, First Office Action, Chinese Application for Invention No. 201580016543.5, dated Jun. 6, 2018, in 15 pages.
European Search Report and Written Opinion for Application No. PCT/IB2015/052257, dated Oct. 17, 2017, in 8 pages.
European Supplementary Search Report for Application No. for PCT/NZ2010000260 dated Feb. 26, 2015, 5 pages.
Japanese Patent Office, Second Official Action, Application No. JP 2016-559289, dated June 21, 2019, in 2 pages.
SIPO Notification of First Office Action (PCT in National Phase) for Application No. 201080063516.0 dated May 6, 2014, 7 pages.
SIPO Second Office Action for Application No. 201080063516.0 dated Feb. 17, 2015, 4 pages.
International Search Report for International Application No. PCT/NZ2010/000260; dated Apr. 27, 2011; 6 pages.
http://en.wikipedia.org/wiki/Oxygen_therapy. Viewed on Jan. 29, 2021.

* cited by examiner

PRESSURIZING MASKS, SYSTEMS AND METHODS

INCORPORATION BY REFERENCE TO ANY PRIORITY APPLICATIONS

This application is a continuation of U.S. patent application Ser. No. 15/128,906, filed Sep. 23, 2016, which is a national phase entry of PCT Application No. PCT/IB2015/052257, which claims priority from, U.S. Provisional Patent Application No. 61/971,464, filed Mar. 27, 2014, the entirety of which is incorporated by reference herein. Any and all applications for which a foreign or domestic priority claim is identified in connection with the present application are hereby incorporated by reference.

BACKGROUND

Field

The present disclosure generally relates to a respiratory mask for use in combination with a nasal high flow cannula. More particularly, the present disclosure relates to a mask that covers nasal high flow cannula to provide an increased or controlled expiratory pressure.

Description of Related Art

One method of treating respiratory distress and certain respiratory disorders, including Chronic Obstructive Pulmonary Disease (COPD) and Obstructive Sleep Apnea (OSA), is the provision of Continuous Positive Airway Pressure (CPAP) to support a user's respiratory system. Non-invasive respiratory pressurization is commonly administered by delivering pressurized breathing gases to a user's mouth and/or nose.

CPAP treatment is usually provided by a breathing assistance system. Breathing assistance systems generally incorporate a source of pressurized gases (potentially a compressor, pressurized gas canister or hospital compressed air supply) and an interface configured to deliver the pressurized gases to a user. Additionally, breathing assistance systems may incorporate a humidifier for heating and humidifying the breathing gases prior to delivery to the user.

Other supported breathing systems include ventilators and respirators. These may adjust pressure between inspiratory and expiratory phases of the breathing cycle, and typically include a return line for the interface.

Conventional interfaces are configured to form a seal with the user's face or upper airway to facilitate adequate pressurization of the user's respiratory system. Forma™ Simplus™, Oracle™, Zest™, Eson™ Opus™, and Pilairo™ are examples of sealing respiratory user interfaces produced by Fisher & Paykel Healthcare. These interfaces are configured to seal with one or more of a user's face, mouth, nose and nares.

The seal formed between the interface and user's respiratory system allows the mask pressure to be regulated by reducing gas leaks and providing a controlled breathing gases exhaust. Gases may be exhausted from the user interface directly to the surrounding atmosphere (through outlet vents) or to another component in the breathing assistance system responsible for controlling the exhaust of breathing gas.

Non-sealing interfaces, particularly nasal cannula, are often employed for supplemental oxygen therapy. Typical supplemental oxygen therapy interfaces deliver flow rates up to 5 l/min directly to the user's nares. Air from the user's surroundings is entrained with the oxygen during normal inhalation, resulting in an increased oxygen concentrations being received by the user's lungs.

Common supplemental oxygen therapy interfaces are supported by a pair of delivery lumen that loop over the users ears. The lumen have small diameters (typically, but not limited to, a range of 0.5-7 mm) and supply oxygen to both sides of the nasal cannula, providing even flow to each nasal prong.

Facial masks are traditionally used for high flow (HF) oxygen therapy. HF oxygen therapy involves providing a flow of oxygen to the nares of a user at flow rates greater than traditional supplemental oxygen therapy. For example, flow rates of HF oxygen therapy can be within a range of 6-60 L/min. Non-sealing HF nasal cannula, such as Fisher & Paykel Healthcare's Optiflow™ Nasal Cannula, are also being promoted for flow rate based treatments (including HF oxygen therapy) where respiratory system pressure regulation can only be imprecisely controlled because the cannula is non sealed.

SUMMARY

Direct delivery of breathing gases to a user's nares can be advantageous as the gases can be administered at a greater temperature and humidity than viable with facial masks. Additionally, direct delivery of the breathing gases allows exhaled gasses to be cleared at the end of expiration, thereby lowering anatomical dead-space. Other advantages of nasal HF therapy are that users can eat and drink whilst wearing a cannula and cannulas are much smaller and lower profile than typical positive pressure interfaces, thus making them less invasive. However, nasal cannulas are not always suitable for users that experience respiratory distress, including hyperventilation, as they do not provide pressure support.

The systems, methods and devices described herein have innovative aspects, no single one of which is indispensable or solely responsible for their desirable attributes. Without limiting the scope of the claims, some of the advantageous features will now be summarized. An object of at least one embodiment is to provide a respiratory mask capable of being applied to a patient's face in combination with a nasal cannula, to deliver high flow therapy with increased or controlled expiratory pressure or to provide the industry or public with a useful choice.

In some configurations, a respiratory mask is configured to overlay a nasal cannula fitted to a user's face. The mask includes a cushion configured to seal with a user's face, allowing a breathing cavity or interior space of the mask to be pressurized. Pressurization of the mask allows for expiratory pressure to be increased or controlled, which may help to treat respiratory distress in COPD patients receiving HF therapy via nasal cannula. The mask is configured to be secured to the user independently of the nasal cannula, thus allowing increased expiratory pressure to be selectively applied. Preferably, the sealing cushion of the mask can include recesses or cut-outs that substantially fit the geometry of a nasal cannula. The mask can include one or more one-way valves that allow entrainment of ambient air during inhalation.

In some configurations, an interface system comprises a nasal cannula having a cannula body. At least one nasal prong extends from the cannula body. A gases tube communicates with the at least one nasal prong. A cannula retention arrangement is coupled to the cannula body and retains the nasal cannula on the head of a user. A mask has a mask body, which defines a user-contacting surface and an interior space when the user-contacting surface is in contact with a face of the user. The mask further comprises a mask retention arrangement that is coupled to the mask body and retains the mask on the head of the user. The interior space of the mask accommodates at least a portion of the cannula body including the at least one nasal prong when the mask is positioned on the head of the user with the user-contacting surface in contact with the face of the user.

In some configurations, the mask is adapted to create a seal around the nose and/or mouth of the user when the mask is used in combination with the nasal cannula and when the user-contacting surface is in contact with the face of the user, the seal being sufficient to provide increased expiratory pressure relative to use of the nasal cannula without the mask. In some such configurations, the mask is also adapted to create a seal around the nasal cannula when the mask is used in combination with the nasal cannula and when the user-contacting surface is in contact with the face of the user, the seal around the nose and/or mouth and the seal on the nasal cannula being sufficient to provide increased expiratory pressure relative to use of the nasal cannula without the mask.

In some configurations, the mask body comprises a frame, wherein the mask retention arrangement is coupled to the frame.

In some configurations, the mask retention arrangement comprises a mask headgear.

In some configurations, the cannula retention arrangement comprises a cannula headgear. In some configurations, the cannula headgear comprises a strap that, in use, extends around the head of the user.

In some configurations, the cannula body comprises a pair of side arms on opposing sides of the cannula body, wherein the cannula headgear is coupled to each of the pair of side arms.

In some configurations, the mask body comprises at least one recess adapted to allow the nasal cannula to extend from within the interior space to outside of the interior space.

In some configurations, the at least one recess is adapted to accommodate the gases tube.

In some configurations, the at least one recess comprises a semi-circular profile.

In some configurations, the at least one recess comprises a portion shaped to correspond to a shape of the gases tube.

In some configurations, the at least one recess is located in a lateral portion of the mask body.

In some configurations, the mask body comprises a cushion that defines the user-contacting surface, wherein the at least one recess is at least partially defined by the cushion.

In some configurations, the at least one recess interrupts the user-contacting surface.

In some configurations, the at least one recess comprises a first recess on a first side of the mask and a second recess on a second side of the mask. In some configurations, a shape and/or size of the first and second recesses are different from one another.

In some configurations, the mask comprises a one-way valve that opens to allow air to enter the interior space of the mask and closes to inhibit air from exiting the interior space of the mask.

In some configurations, the valve can be biased or pre-loaded to a slightly open position. In some such configurations, the valve can move from the biased, pre-loaded or normal position to the closed position in response to expiration by the user.

In some configurations, the mask comprises a vent that allows pressure within the interior space of the mask to be released.

In some configurations, the vent is manually operable.

In some configurations, an effective size of the vent is variable.

In some configurations, the mask further comprises a bias flow vent.

In some configurations, the mask further comprises a condensation vent that permits water to be evacuated from the interior space of the mask.

In some configurations, the mask further comprises a pressure port that communicates with the interior space and allows measurement of a pressure within the interior space.

In some configurations, the mask further comprises a positive end expiratory pressure valve that opens at or above a threshold pressure within the interior space of the mask.

In some configurations, a mask is configured for use in combination with a nasal cannula or other unsealing or high flow interface. The mask can be applied and removed from a user separately from the nasal cannula. The nasal cannula has a cannula body, at least one nasal prong that extends from the cannula body, a gases tube that communicates with the at least one nasal prong and a cannula headgear that is coupled to the cannula body and retains the nasal cannula on the head of a user. The mask comprises a mask body. The mask body defines a user-contacting surface and an interior space when the user-contacting surface is in contact with a face of the user. The mask further comprises a mask retention arrangement that is coupled to the mask body and retains the mask on the head of the user. The interior space of the mask accommodates at least a portion of the cannula body including the at least one nasal prong when the mask is positioned on the head of the user with the user-contacting surface in contact with the face of the user. The mask body comprises at least one recess adapted to allow the nasal cannula to extend from within the interior space to outside of the interior space, wherein the at least one recess interrupts the user-contacting surface.

In some configurations, the mask is adapted to create a seal around the nose and/or mouth of the user when the mask is used in combination with the nasal cannula and when the user-contacting surface is in contact with the face of the user, the seal being sufficient to provide increased expiratory pressure relative to use of the nasal cannula without the mask. In some such configurations, the mask is also adapted to create a seal around the nasal cannula when the mask is used in combination with the nasal cannula and when the user-contacting surface is in contact with the face of the user, the seal around the nose and/or mouth and the seal on the nasal cannula being sufficient to provide increased expiratory pressure relative to use of the nasal cannula without the mask.

In some configurations, the mask body comprises a frame, wherein the mask retention arrangement is coupled to the frame.

In some configurations, the mask retention arrangement comprises a mask headgear.

In some configurations, the at least one recess is adapted to accommodate the gases tube.

In some configurations, the at least one recess comprises a semi-circular profile.

In some configurations, the at least one recess comprises a portion shaped to correspond to a shape of the gases tube.

In some configurations, the at least one recess is located in a lateral portion of the mask body.

In some configurations, the mask body comprises a cushion that defines the user-contacting surface, wherein the at least one recess is at least partially defined by the cushion.

In some configurations, the at least one recess comprises a first recess on a first side of the mask and a second recess on a second side of the mask. In some configurations, a size and/or shape of the first and second recesses are different from one another.

In some configurations, the mask comprises a one-way valve that opens to allow air to enter the interior space of the mask and closes to inhibit air from exiting the interior space of the mask.

In some configurations, the valve can be biased or pre-loaded to a slightly open position. In some such configurations, the valve can move from the biased, pre-loaded or normal position to the closed position in response to expiration by the user.

In some configurations, the mask comprises a vent that allows pressure within the interior space of the mask to be released.

In some configurations, the vent is manually operable.

In some configurations, an effective size of the vent is variable.

In some configurations, the mask further comprises a bias flow vent.

In some configurations, the mask further comprises a condensation vent that permits water to be evacuated from the interior space of the mask.

In some configurations, the mask further comprises a pressure port that communicates with the interior space and allows measurement of a pressure within the interior space.

In some configurations, the mask further comprises a positive end expiratory pressure valve that opens at or above a threshold pressure within the interior space of the mask.

In some configurations, a method of providing respiratory support to a patient includes applying a nasal cannula to the patient, providing a flow of gas to the nares of the patient through the nasal cannula, and selectively applying a mask to the patient over the nasal cannula, wherein the mask comprises an interior space that accommodates the nasal cannula and wherein the mask creates a seal on the face of the patient, to increase an expiratory pressure relative to use of the nasal cannula without the mask.

In some such configurations, the method further comprises allowing air to enter the interior space of the mask through a one-way valve.

In some such configurations, the method further comprises relieving the pressure within the interior space by opening a vent.

In some such configurations, the method further comprises allowing air to exit the interior space of the mask through a one-way valve when the pressure within the interior space is at or above a threshold value.

In some such configurations, the method further comprises selectively removing the mask from the patient without removing the nasal cannula.

In some configurations, any of the above-described systems or methods can replace the nasal cannula with another unsealing or high flow interface.

In some configurations, any of the above-described systems, masks or methods can replace the mask with another suitable sealing interface capable of accommodating the unsealing or high flow interface.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

DETAILED DESCRIPTION

Figure 1:
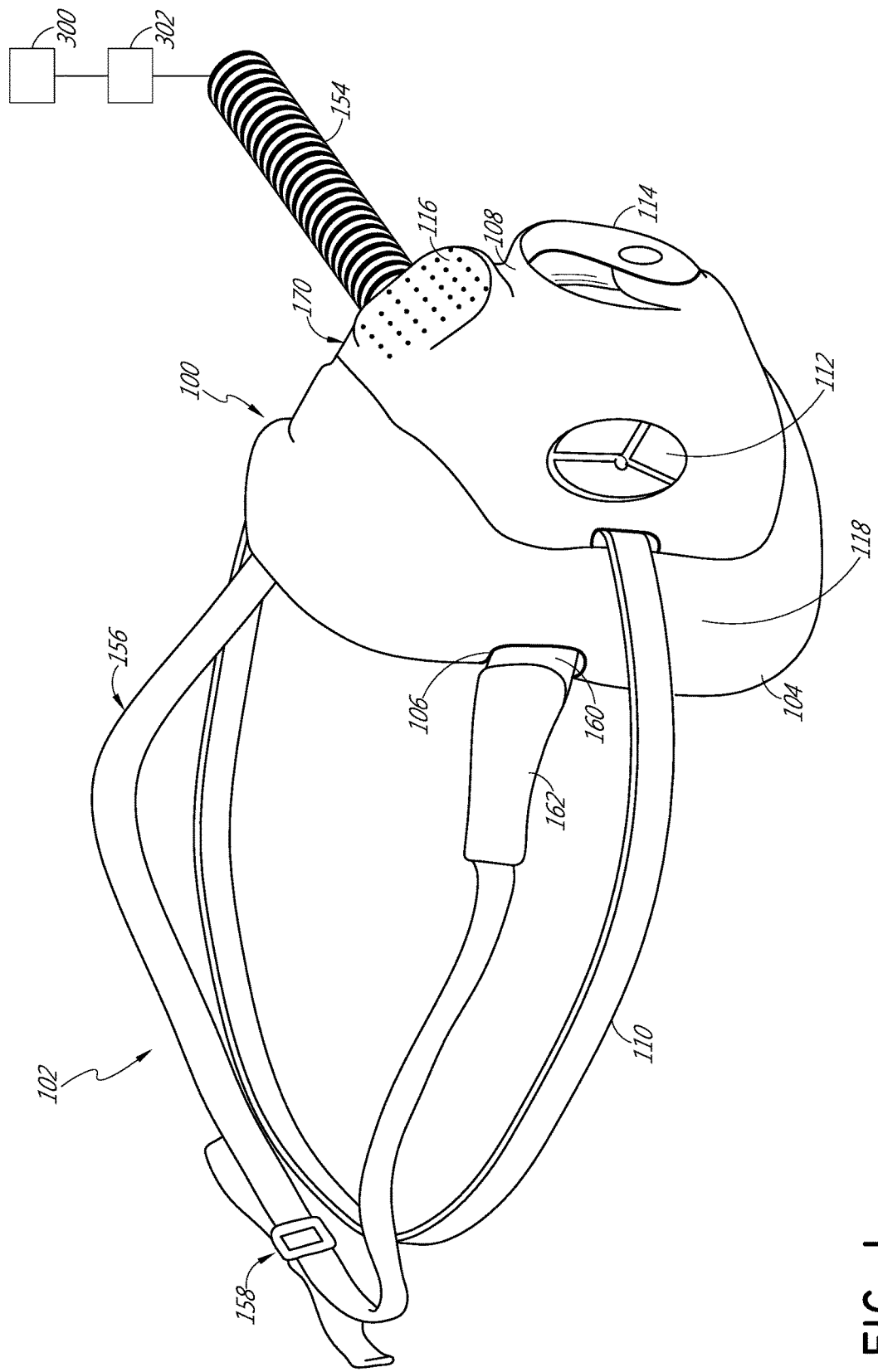
FIG. 1 is a perspective view of a mask having certain features, aspects or advantages of a preferred embodiment overlaying a nasal cannula.

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" refer to directions in the drawings to which reference is made. Terms such as "front," "back," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

Common treatments for respiratory diseases, such as COPD and OSA, include, but are not limited to, CPAP, supplemental oxygen therapy and HF therapies. These therapies all have advantages and disadvantages. The masks disclosed herein, when used in combination with a nasal cannula, may be able to provide users or patients with the benefits of combined therapies. More specifically, the disclosed masks or systems may allow the provision of gases at higher temperatures and/or humidity levels, such as a nasal cannula can supply, and the increased respiratory pressures required or desirable for the treatment of respiratory distress.

Figure 2:
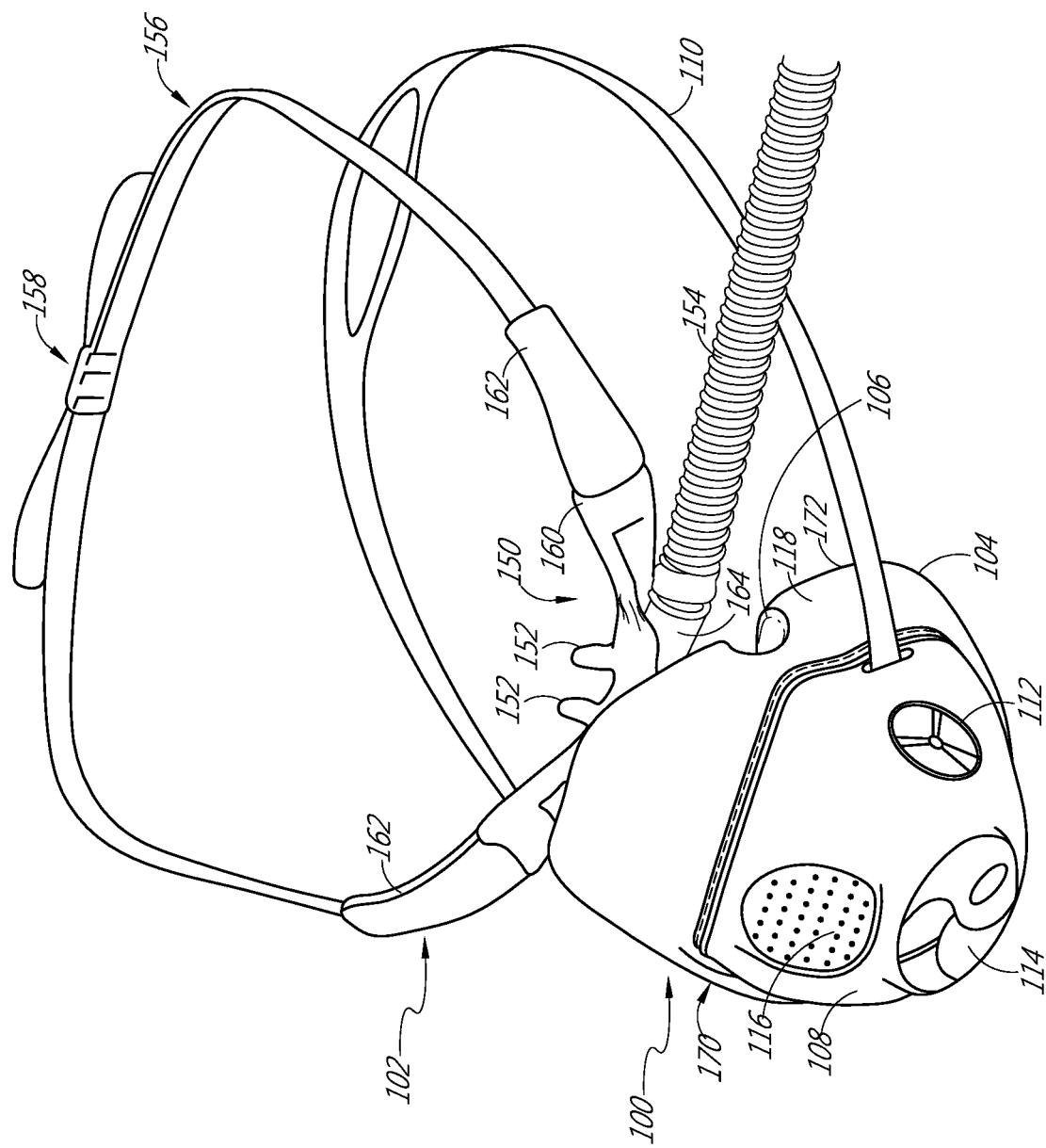
FIG. 2 is an exploded view of the mask and a nasal cannula of FIG. 1.

FIG. 1 is a perspective view of an embodiment of a mask 100 overlaying a nasal cannula 102. FIG. 2 shows an exploded view of the same mask 100 and nasal cannula 102 set-up. As described above, in some applications, the nasal cannula 102 can provide the flow of breathing gas to the user. Thus, the nasal cannula 102 can be applied to the user separately from the mask 100. The mask 100 can be selectively applied to the user without removal of the nasal cannula 102 and, preferably, without significant movement or other manipulation of the nasal cannula 102. Similarly, the mask 100 preferably can be removed from the user without removal of the nasal cannula 102 and, preferably, without significant movement or other manipulation of the nasal cannula 102. Although a nasal cannula 102 is illustrated herein, other suitable interfaces can be used to deliver the flow of breathing gas to the user, including, for example but without limitation, other suitable high flow therapy interfaces. Such interfaces preferably are unsealing interfaces that do not create an airtight seal or a substantially airtight seal with the user. For example, a high flow therapy can be delivered via an oral interface or a tracheal interface instead of the nasal cannula 102, and pressure support can be augmented by placing a mask 100 or other interface over that oral or tracheal interface. Therefore, references to nasal cannula 102 herein can also refer more generally to other suitable unsealing or high flow interfaces, unless otherwise indicated explicitly or by the context of the disclosure.

In some configurations, the mask 100 is specially shaped or configured to accommodate the nasal cannula 102 and allow the nasal cannula 102 to extend from within the mask 100 to outside of the mask 100 while being capable of creating a sufficient seal with the user's face to provide increased pressure within the mask 100. As a result, use of the mask 100 in combination with the nasal cannula 102 allows the respiratory pressure within the user's airways to be elevated relative to the pressure when using the nasal cannula 102 without the mask 100. As described above, such an arrangement can help to treat respiratory distress in, for example, COPD patients receiving HF therapy via the nasal cannula 102.

The mask 100 and nasal cannula 102 can be sold as a system or kit, in which the mask 100 and nasal cannula 102 are sold together or in a single package. In other configurations, the mask 100 can be configured for use in combination with one or more particular models of nasal cannula, but can be sold separately from such nasal cannula. In some configurations, the mask 100 can be configured for use in combination with a broad spectrum of nasal cannula; however, in order to accommodate many different nasal cannula shapes and designs, the ability of the mask 100 to create an optimal seal with at least a portion of the nasal cannula may be compromised. Nonetheless, such a general purpose mask can create a seal that is sufficient to provide pressure support to the user. In some configurations, the mask 100 and nasal cannula 102 are at least designed, if not sold, as a system.

The nasal cannula 102 can be of any suitable configuration for the intended use, such as HF nasal therapy. The nasal cannula 102 can have a body 150 from which at least one nasal prong 152 extends. In the illustrated arrangement, a pair of nasal prongs 152 is provided. Preferably, when the nasal cannula 102 is properly positioned on the user's head, the nasal prongs 152 extend toward or into, but do not fully seal with, the user's nares.

The nasal cannula 102 includes a gases or breathing circuit that communicates with the nasal prongs 152. In the illustrated arrangement, the gases circuit comprises at least one gases tube 154 that supplies a flow of breathing gas to the nasal prongs 152 and, thus, can be referred to as a supply tube. In the illustrated arrangement, a single supply tube 154 is provided and extends to one side of the nasal cannula 102. In other arrangements, the supply tube 154 can extend in other directions and/or multiple supply tubes 154 can be provided. For example, in some configurations, a supply tube 154 can be provided on and extend to each side of the nasal cannula 102. In use, the supply tube 154 can be connected to a source of pressurized gases 300 and, optionally, a humidifier 302. The source of pressurized gases 300 can be configured to supply supplemental oxygen to the user. Any suitable source of pressurized gases 300 can be used.

The nasal cannula 102 preferably also includes a retention or headgear arrangement that secures or retains the nasal cannula 102 onto the user's head. In the illustrated cannula 102, the headgear arrangement is in the form of a single strap 156 that extends around the user's head from one side of the cannula body 150 to the other side of the cannula body 150. However, in other configurations, the headgear arrangement can more complex, such as including multiple straps or multiple strap portions. The headgear arrangement can include a rear portion that extends around the back of the user's head and/or an upper portion that extends over the top of the user's head. The headgear arrangement can include flexible or relatively rigid portions, elastic or relatively inelastic portions or any combination thereof.

Preferably, the headgear arrangement includes one or more adjustment portions or adjustment mechanisms 158 that permit adjustment of a length or size of the headgear arrangement. The adjustment mechanism 158 can be of any suitable arrangement, such as any multi-position connector, and can have discrete adjustment positions or can be infinitely adjustable. For example, the adjustment mechanism 158 can include a strap or strap portion forming or having one or more adjustment loops or overlapping portions that can be adjusted in size via a sliding buckle or hook-and-loop fastener, for example. Other suitable arrangements, such as multi-position snap closures, for example, can also be used.

In other configurations, the nasal cannula 102 can include other arrangements for securing or retaining the nasal cannula 102 on the user's head. For example, the nasal cannula 102 can comprise 'loop' pads on patient-facing surfaces of the cannula body 150 that can interface with complementary 'hook' pads adhered to the face of the user (e.g., for a 'hook-and-loop' style connection), or vice-versa. As a second example, the nasal cannula 102 could be connected to a helmet, bonnet or coif-style headwear adapted to secure or retain the nasal cannula 102 on the head. As a third example, a portion of the nasal cannula 102 (including but not limited to the cannula body 150) could be adhered directly to the face (using, for example, a resealable adhesive structure). In some configurations, the headgear or other retention arrangement of the nasal cannula 102 is separate from the headgear or other retention arrangement of the mask 100, or at least is capable of retaining the nasal cannula 102 on the user's head without assistance or reliance on the headgear or other retention arrangement of the mask 100.

In the aforementioned or other respects, the nasal cannula 102 can be of any suitable arrangement for the desired use. For example, the cannula body 150 can comprise a frame 160 that supports the nasal prong(s) 152. The nasal prong(s) 152 can be unitarily formed with the frame 160 or can be a separate component(s) that is permanently or removably secured to the frame 160. In the illustrated arrangement, the nasal prongs 152 and frame 160 are a unitary structure that is formed by, for example, injection molding.

The illustrated frame 160 is a generally elongate structure that extends in a lateral direction across the upper lip and toward or onto the cheeks of the user. The nasal prong 152 extends upwardly from a central portion of the frame 160. The frame 160 can be made from a relatively soft, resilient material such that the frame 160 can generally hold its shape in the absence of external forces applied to the frame 160, but can also generally conform to the face of the particular user. For example, a soft, flexible material such as silicone, other cannula material known in the art or other suitable materials can be used.

In some configurations, the head strap 156 can be coupled to lateral end portions of the frame 160 by any suitable connector, such as a clip 162 having a locking tab or other locking member that engages a slot or other locking surface of the frame 160. The clips 162 can be formed at least in part from or can include a covering sleeve made from a soft material (e.g., silicone) to provide comfort to the user and/or enhance the grip of the clips 162 on the user's face.

In some configurations, the frame 160 can be configured to receive a manifold 164 that is connected to the supply tube 154 and delivers a flow of gas from the supply tube 154 to the nasal prong(s) 152. The manifold 164 can be constructed of a material that is relatively rigid or more rigid than the material of the frame 160 and/or nasal prong(s) 152. For example, in some configurations, the manifold 164 is constructed in whole or in part from polycarbonate, high-density polyethylene (HDPE) or another suitable material. The manifold 164 can include one or more openings or ports that allow communication of a flow of breathing gases from the supply tube 154 to the nasal prong(s) 152 via the manifold 164. One example of a suitable nasal cannula 102 is disclosed in Applicant's Publication No. WO2014/182179, entitled PATIENT INTERFACE AND HEADGEAR FOR A RESPIRATORY APPARATUS, the entirety of which is hereby incorporated by reference herein and made a part of the present disclosure.

The illustrated mask 100 includes a sealing cushion 104, one or more cannula cut-outs 106, a mask frame 108, a headgear arrangement or head strap 110, a one-way valve 112, a variable vent 114 and a fixed bias flow vent 116. Unlike non-invasive respiratory masks known in the art, the illustrated mask 100 may not include an air supply conduit or connection port. Instead, a portion or most of the air flow to the user is supplied by the nasal cannula system 102 with any deficit being supplied through the one-way valve(s) 112. With such an arrangement, the mask 100 can act as a pressure vessel that can increase the expiratory pressure within the airways of the user.

The mask 100 can comprise a mask body 170, which can be made up of, in whole or in part, the mask frame 108 and the sealing cushion 104. The sealing cushion 104 can be referred to herein as a "seal" or as a "cushion." The mask frame 108 can be unitary with or can support the cushion 104. In the illustrated arrangement, the mask frame 108 and the cushion 104 are separate components or at least formed in separate steps. The mask frame 108 can be constructed from a material that is capable of at least substantially maintaining its shape in the absence of external forces applied to the mask frame 108. In some configurations, the mask frame 108 can be resilient. In other configurations, the mask frame 108 can be relatively rigid or more rigid than the cushion 104. For example, the mask frame 108 can be constructed in whole or in part from polycarbonate, high-density polyethylene (HDPE) or another suitable material. The mask frame 108 can be a one-piece structure or can be a multi-piece structure. For example, a first mask frame portion or element can support the cushion 104 and a second mask frame portion or element can provide for connection of the headgear 110. The first mask frame portion and the second mask frame portion can be permanently or, preferably, removably connected to one another.

The cushion 104 can be configured to provide an interface between the user and the mask 100 and can be made from a flexible material, such as silicone rubber, a thermoplastic elastomer or any other suitable seal material. The cushion 104 can be secured to the mask frame 108 by any suitable process or arrangement. For example, the cushion 104 can be removably coupled to the mask frame 108, such as by a flange-and-groove arrangement. In other configurations, the cushion 104 can be attached to the mask frame 108 by adhesives or during the forming process (e.g., overmolding or co-molding).

The cushion 104 preferably includes one or more features configured to accommodate the nasal cannula 102 when the mask 100 is applied to a user while the nasal cannula 102 is in use. For example, the cushion 104 can include at least one cannula recess or cut-out 106. In other configurations, the cushion 104 can include other configurations to accommodate the nasal cannula 102, such as regions of increased compliance or thin-walled regions that allow the cushion 104 to stretch over the nasal cannula 102. Such thin-walled regions may have a wall thickness that is significantly thinner than surrounding portions of the cushion 104 and may be sized and/or shaped to generally correspond to the size and/or shape of the portion of the nasal cannula 102 that passes underneath the cushion 104. Examples of thin-walled regions are described in Applicant's PCT Application No. PCT/NZ2015/050019, filed Feb. 26, 2015, entitled "RESPIRATORY MASK WITH NASOGASTRIC TUBE PATH," the entirety of which is incorporated by reference herein and made a part of the present disclosure. In the illustrated arrangement, the cushion 104 includes a cannula cut-out 106 on each side of the mask 100. In particular, the illustrated cushion 104 includes a cut-out 106 on each lateral side of the mask 100. The cut-outs 106 can be configured to accommodate, complement or match the lateral geometry of a nasal cannula, in general, or a particular nasal cannula 102. Such an arrangement enables a cannula to pass between the mask 100 and a user's face, preferably with minimal or acceptable gaps between the cannula and mask 100. Preferably, when properly positioned on the user in combination with the nasal cannula 102, the mask 100 can create a seal with the face of the user that is sufficient to allow for an increase in pressure within an interior space or breathing cavity of the mask 100 and/or an increased expiratory pressure within the user's airways relative to the use of the nasal cannula 102 without the mask 100. In some configurations, the mask 100 also creates at least a substantial seal with the nasal cannula 102. The combination of the seal with the user's face and with the nasal cannula 102 is sufficient to allow for an increase in pressure within an interior space or breathing cavity of the mask 100 and/or an increased expiratory pressure within the user's airways. Accordingly, descriptions of a seal between the mask 100 and the user's face herein can include the seal between the mask 100 and the nasal cannula 102 unless otherwise indicated. In some configurations, the mask 100 is capable of creating a seal with the user's face that is sufficient to allow for a therapeutically-significant increase in an increase in pressure within an interior space or breathing cavity of the mask 100 and/or an increased expiratory pressure within the user's airways relative to the use of the nasal cannula 102 without the mask 100.

As described herein, mask 100 can be configured for use with a particular nasal cannula or several particular nasal cannula. For example, the mask 100 can be configured for use with the nasal cannula 102 shown and described herein. In some configurations, the cut-outs 106 can be configured to accommodate portions of the nasal cannula 102 that pass between the cushion 104 and the user's face when the mask 100 is used in combination with the nasal cannula 102.

The cut-outs 106 can have a shape or profile that approximates, is complementary to or closely matches a shape of the portion of the nasal cannula 102 that passes through the cut-out 106. In some configurations, the cut-outs 106 can simply accommodate or approximate the shape of the nasal cannula 102 and the mask 100 can rely on the ability of the material of the cushion 104 to stretch or conform to the shape of the nasal cannula 102. In other configurations, the cut-outs 106 can closely follow or substantially match the shape of the nasal cannula 102.

The cushion 104 can be shaped, sized or otherwise configured to encompass a user's nose and/or mouth. The cushion 104 can have a side wall 118, which can have a substantially triangular shape or profile. The side wall 118 can have a first end that is proximal to the user's face and transitions into a sealing surface or a user-contacting surface 172 that contacts the user's face. The sealing surface 172 extends, in a substantially perpendicular direction, from the side wall 118 towards the center of the mask 100. The cannula cut-outs 106 can take the form of stepped regions in the sealing surface 172. In some configurations, the cut-outs 106 create a gap in a sealing surface 172 of the cushion 104. That is, end portions of the cut-outs 106 can be spaced from one another in a direction that traces a perimeter of the sealing surface 172.

Nasal cannulas typically extend laterally from the underside of a user's nose, across the user's cheeks towards the user's ears. As described herein, the geometry of the surface of the cushion 104 within the cut-outs 106 can be configured to match the geometry of the nasal cannula that extends beneath the mask's sealing surface. Depending on the particular nasal cannula used in combination with the mask 100, this may require or make it desirable that the shape or geometry of the cut-outs 106 is different on each side of the cushion 104. For example, if the cannula has an asymmetric air supply as in the cannula 102 of FIGS. 1 to 4, the shape or geometry of the cut-outs 106 may also be asymmetrical. In the illustrated arrangement, as shown in FIG. 1, a portion of the frame 160 of the nasal cannula 102 passes between the cushion 104 and the user's face on one side of the mask 100. On that side, the cut-out 106 has a generally rectangular profile or shape that generally corresponds to the shape of the portion of the frame 160 that underlies the cushion 104. On the other side of the mask 100, a portion of the frame 160 and the supply tube 154 passes between the cushion 104 and the user's face, as shown in FIG. 2. On that side, the cut-out 106 comprises a generally semi-circular profile or shape that generally corresponds to the shape of the supply tube 154. The cut-out 106 on the tube 154 side can also include a generally rectangular portion such that the cut-out 106 overall generally corresponds to the shape of the combination of the frame 160 and supply tube 154.

In some configurations, one or more one-way valves 112 are provided on the mask 100, such as within the mask frame 108. The one-way valve(s) 112 can be configured to open on inhalation by the user, allowing for entrainment of ambient air along with the air supplied by the nasal cannula 102, and at least partially close to restrict flow on exhalation by the user in order to maintain the increased pressure within the mask 100. The entrainment of ambient air helps to ensure that the user's inspiratory flow requirements are met, by reducing inspiratory resistance. The one-way valve(s) 112 can remain closed on exhalation, thus restricting air flow between the inside of the mask 100 and the atmosphere, thus increasing the resistance to expiration and pressure within the user's airways. Increased respiratory pressure and expiratory resistance can help to reduce user's breathing rates. In some configurations, the valve(s) 112 can remain somewhat open in the absence of inhalation by the user instead of being completely closed. The valve(s) 112 can be pre-loaded or biased to a slightly open position, thus allowing ambient gases to pass through the valve(s) 112 and into the mask 100. It is presently believed that it could be useful, particularly for very sick patients, to require a lower amount of force to open the valve 112 on inspiration to make sure the patient is properly ventilated, even if pressure support might be slightly decreased as a result. In some configurations, the one-way valve(s) can be configured to move to a closed position from a slightly-opened biased or normal position in response to an appropriate force (e.g., expiration by the user). For example, the bias can be selected so that 1-5 cm of gas pressure moves the valve 112 toward or to the closed position, thereby increasing pressure in the mask. In some configurations, the one or more valves 112 can be located on the lateral sides of the mask frame 108; however, in other embodiments, the valves 112 may be located in any other suitable location on the mask 100.

In some configurations, a variable vent 114 is included in the mask 100. In one embodiment, the vent 114 can comprise an opening or open region in the mask frame 108 that can be provided with, for example, a manual mechanism that allows a user to variably open and close the vent 114 by blocking a portion or an entirety of the opening. Thus, an effective size of the opening that permits communication with the atmosphere outside of the mask 100 can be varied, thereby allowing an effective size of the vent 114 to be varied. In other arrangements, the vent 114 may be non-variable and/or may be automatically controlled. The variable vent 114 can enable the application of expiratory pressure to be selectively applied without removal of the mask 100. It is possible that a patient receiving HF therapy may only experience episodes of respiratory distress and, thus, may not need ongoing expiratory pressure support. The presence of a variable vent 114 can allow users and/or medical practitioners to selectively apply and/or variably adjust the amount of pressure provided by the mask 100. When the variable vent 114 is substantially open, breathable gases can at least relatively freely flow in and out of the mask 100 and the pressure inside the mask 100 can be substantially the same as atmospheric pressure.

The ability to remove the pressure support to a user's airways without removing the mask 100 allows users and/or medical practitioners to check whether breathing rates remain stable when the pressure support is removed, without the hassle of removing and refitting the mask 100 if the user is still suffering from respiratory distress. The variable vent 114 can be opened to reduce the internal pressure within the mask 100, and if the user's breathing rate remains stable then the mask can be removed. If, however the user's breathing rate increases then the variable vent 114 can be closed and the internal pressure restored, without the hassle of refitting the mask. Having a variable vent 114 may allow the user to be gradually weaned from the pressure support, by gradually opening the vent 114 to reduce the internal pressure within the mask 100.

Figure 3:
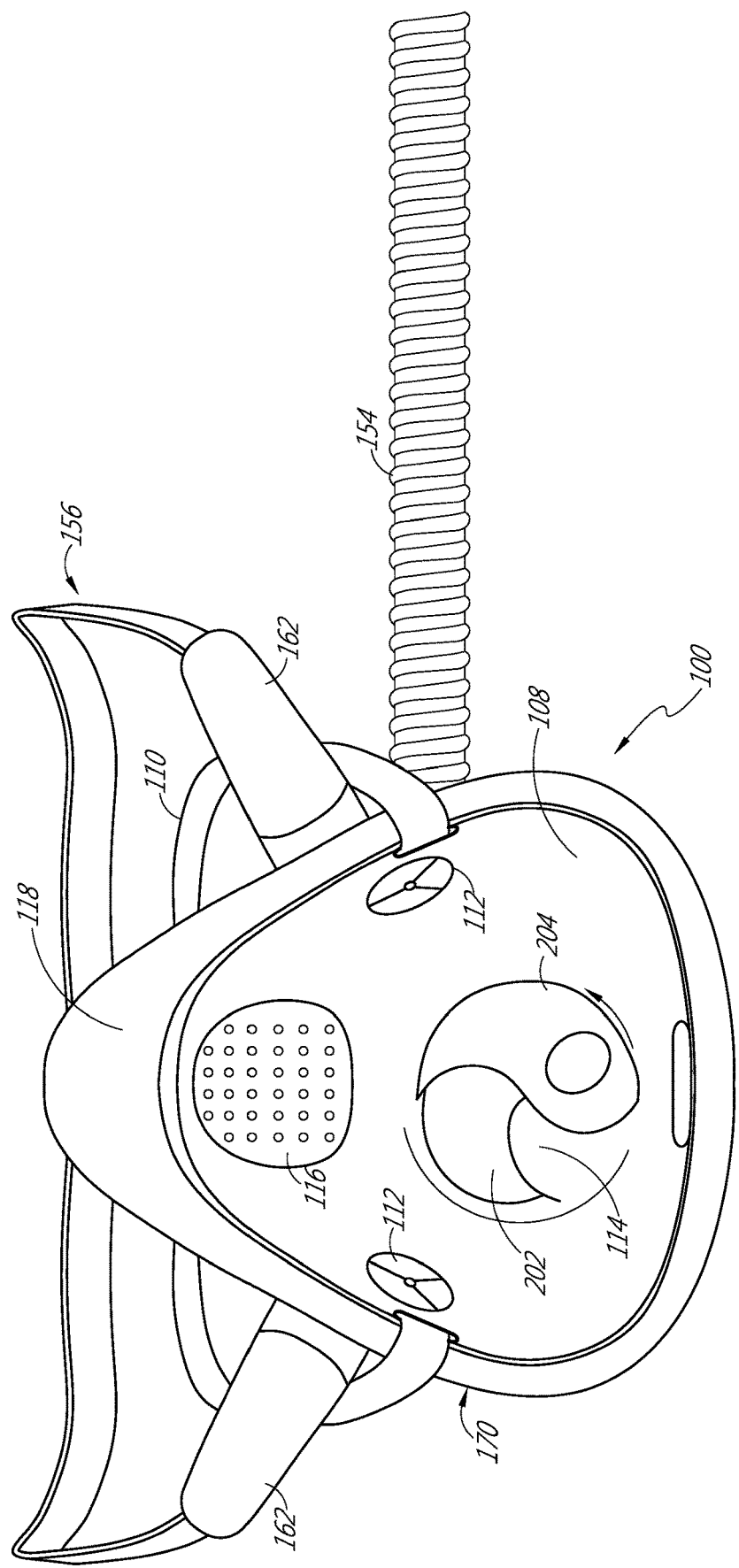
FIG. 3 is a front view of the mask and cannula of FIG. 1.

In some configurations, such as that shown in FIG. 3, the variable vent 114 can be centrally located on the front of the mask 100. This location can be beneficial in allowing for easy access and manipulation of the vent 114 by the user or medical practitioner. In some configurations, the vent 114 can comprise a semicircular outlet 202 that can be partially or completely concealed by a rotatable cover 204. In alternative embodiments, there can be one or more vent outlets of any suitable shape that can be variably covered. The vent cover may be configured to move in a variety of ways including, but not limited to, planar sliding, hinged motion or the removal of a completely separate cap.

In some configurations, the mask 100 includes one or more fixed bias flow vents 116. The bias flow vent 116 may take any suitable form that allows the flow of breathable gases from inside the mask 100 to the atmosphere. This may include, but is not limited to, one or more small holes, a region of porous material, or a gap between the cushion 104 and the cannula 102 or user's face. The bias flow vent 116 provides an exhaust path to flush $CO_2$ from the mask 100. The geometry of the bias flow vent 116 can be selected or configured to allow for a certain flow rate of air to pass through the bias flow vent 116, which can be determined at least in part on the dead space within the mask 100. In the illustrated arrangement, the bias flow vent 116 comprises a series of small holes located in a central position on the mask frame 108. However, in other arrangements, the bias flow vent(s) 116 can be located in any other suitable position on the mask 100.

In some configurations, as discussed herein, the mask 100 can be secured to the user independently of the nasal cannula 102 via a head strap 110 or any other appropriate securement arrangement. Being attached to the user independently of the nasal cannula 102 allows adjustments to the fit of the mask 100 with minimal interference to the fit of the nasal cannula 102. Because the mask 100 is substantially larger than a nasal cannula, it may require higher headgear tensions or greater structural integrity in order to be secured effectively to a user's head and/or face. In the arrangement of FIGS. 1-4, the head strap 110 may be configured to include a single or bifurcated strap, which can be made from an elastic material. Alternatively, the head strap 110 can be made of a substantially inelastic material and can include an adjustment mechanism, such as a buckle or any other appropriate mechanism. In a further arrangement, the mask 100 may be configured to include a headgear that includes multiple straps and adjustment mechanisms, such as but not limited to hook and loop tabs. In other configurations, both the mask 100 and cannula 102 can be specifically designed for use as a system or can be provided as an integrated unit.

Figure 4:
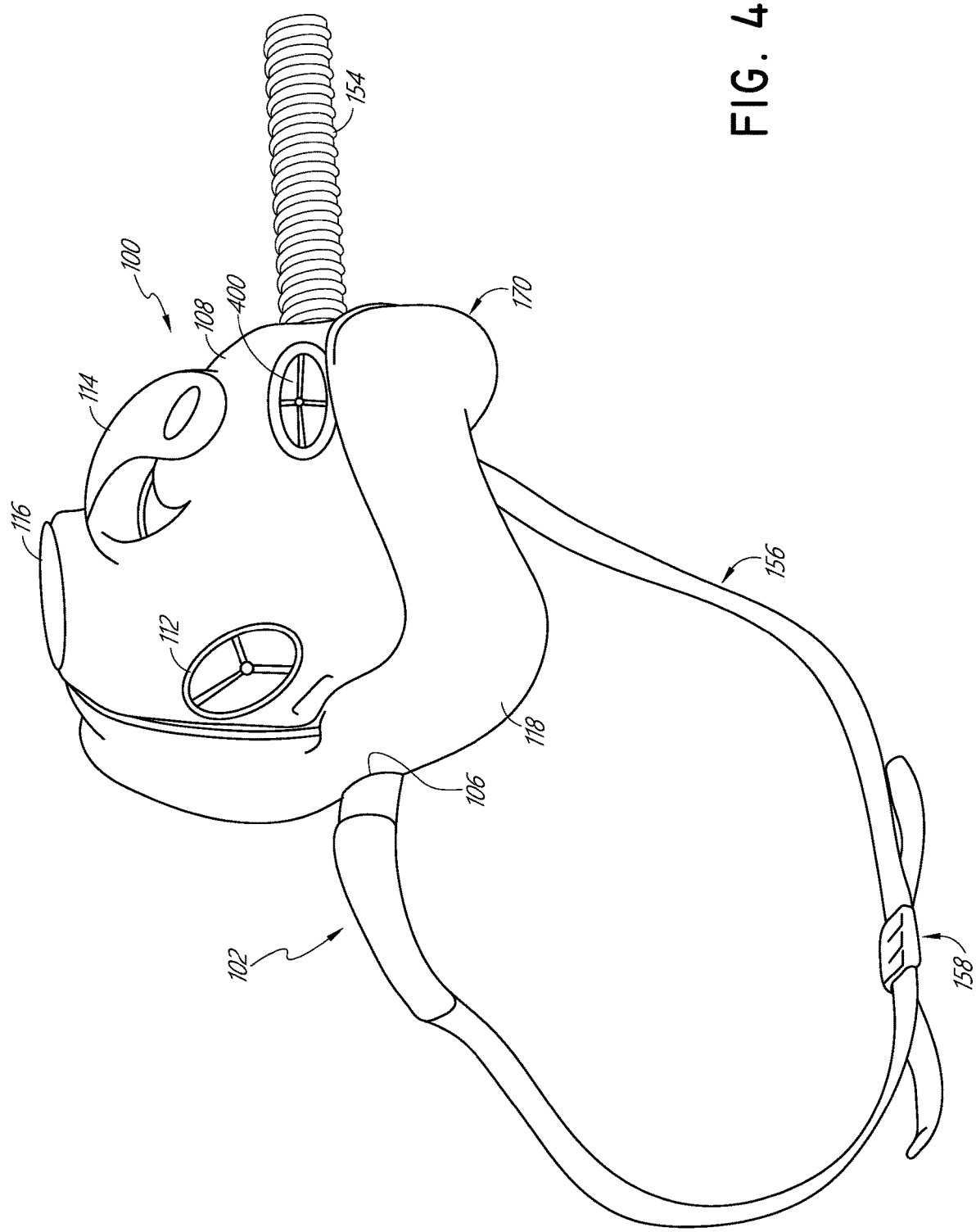
FIG. 4 is a perspective view of the underside of the mask of FIG. 1.

FIG. 4 illustrates the underside of the mask 100. FIG. 4 also shows an additional (optional) vent 400 that can be configured to allow condensation to be released from inside of the mask 100. The gases applied to a patient during HF therapy can have a high temperature and humidity. When combined with the mask 100, it is possible that the high temperature and humidity of the gas will result in the formation of condensation within the mask 100 as a result of restricted airflow out of the mask and the cold surfaces of the mask frame 108. There are several undesirable consequences to having condensation build up within a mask. Some of the consequences include, but are not limited to, interference with the user's therapy, discomfort on user's skin, and the creation of annoying noises. A vent 400 can be provided to the mask 100 to allow condensation to be removed from the mask 100. In some configurations, the vent 400 can be or comprise a one-way valve that opens on inhalation to allow water accumulated in the region of the valve to drain out during inhalation. In another configuration, the vent 400 can be or comprise a one-way valve that opens on exhalation to allow water to be forced out of the mask 100. In this embodiment, the valve can be configured so as not to substantially reduce the internal pressure within the mask 100, when open on exhalation. Alternatively, the vent 400 can be an opening that is sealed with a manually removable plug or cap. The user or a medical practitioner can open the vent 400 as necessary or desired to drain water from the mask 100. In the illustrated configuration, the vent 400 is located on a lower and/or downward facing surface of the mask frame 108. Such an arrangement enables the vent 400 to act as a water trap because gravity will encourage condensation to fall towards the bottom of the mask 100 and, thus, the vent 400. By releasing the water from the bottom of the mask 100, it may be possible to reduce the buildup of condensation without needing to remove the mask 100.

Figure 5:
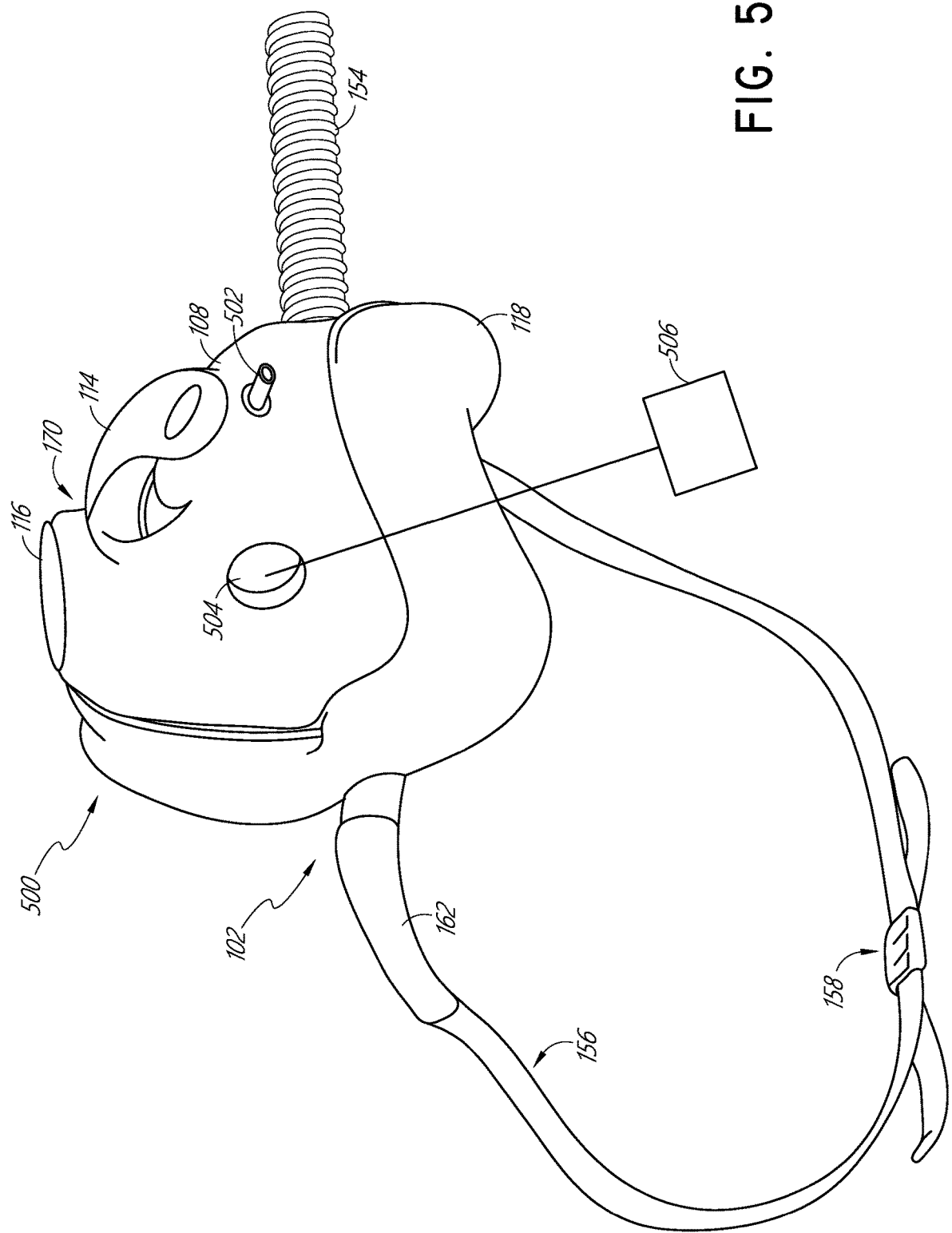
FIG. 5 is a perspective view of the underside of an alternative embodiment of a mask having certain features, aspects or advantages of a preferred embodiment.

FIG. 5 illustrates a view of the underside of an alternative embodiment of a mask 500, which can be the same as or similar to the mask 100 with the exception of the features explicitly described herein. A pressure port 502 can be provided on the mask 500 to allow the pressure inside the mask 500 to be measured. Such an arrangement enables a flow controller to measure the pressure swing between inspiration and expiration. The pressure data from inside the mask 500 can then be used by the flow controller for the cannula 102 to measure respiratory rate and the level of respiratory distress. This information could then be communicated to a display, such as the display on the flow controller, or via USB, Bluetooth or another suitable communication protocol to a computer or phone display to indicate a suitable opening position for the variable vent 114. This position could be manually set by the medical practitioner or in a further embodiment could be automatically controlled by the flow controller to maintain expiratory pressure at a level to achieve a desired respiratory rate. This control may be through an electronic connection between the flow controller and the mask 500 that can enable the control of an automated valve that adjusts the pressure within the mask 500 via controlled venting. The displayed information may also indicate when the mask 500 can be removed, as the patient no longer requires pressure support, and the therapy can continue with the cannula 102 only.

In a further arrangement, rather than controlling the position of a variable vent 114, the motor speed of the flow controller could be altered during inspiration and expiration, to control the pressure within the mask 500 and manage a user's respiratory rate. In this way the effect of opening a variable vent 114 can be automatically simulated by slowing the flow controller motor speed during expiration. The controller may then use pressure measurements from within the mask 500, provided via the pressure port 502, to determine whether the patient respiratory rate is such that the mask 500 can be safely removed with the therapy continuing through the cannula 102 alone. Such an arrangement essentially provides a closed loop system, wherein the flow controller can measure, interpret and influence the breathing rates of a user by modifying flow induced pressure, without the need for interaction from a medical practitioner. In such an arrangement, preferably, the only interaction required by a medical practitioner will be the application and removal of the mask 500.

In some configurations, the mask 500 can additionally or alternatively include a port 504, as shown in FIG. 5, which allows a Positive End Expiratory Pressure (PEEP) Valve 506 to be connected to the mask 500. Any suitable PEEP valve configuration, such as those known in the art, may be used for this purpose. One example of a PEEP valve configuration is incorporated into a connector in Applicant's U.S. Pat. No. 7,341,059, entitled "BREATHING ASSISTANCE APPA- RATUS," the entirety of which is incorporated by reference herein and made a part of the present disclosure. When exhaling, the mask 500 acts as a pressure vessel causing the respiration pressure to increase. The PEEP valve 506 will set a maximum pressure threshold, which when exceeded the PEEP valve 506 will open and vent the above-threshold pressure. When the pressure is at or below the PEEP valve pressure, the valve will close again. Therefore, the mask 500 will allow the generation of positive pressure in the mask 500, airways and lungs while the PEEP valve 506 will limit the maximum expiration pressure developed. The PEEP valve 506 can provide a maximum allowed positive pressure, which may be manually variable, or in some embodiments may be variably controlled by the feedback loop provided by the flow controller, pressure port 502, and an electronic actuator. In a further variation of this arrangement, a PEEP valve 506 can be permanently connected to the mask 500.

Figure 6A:
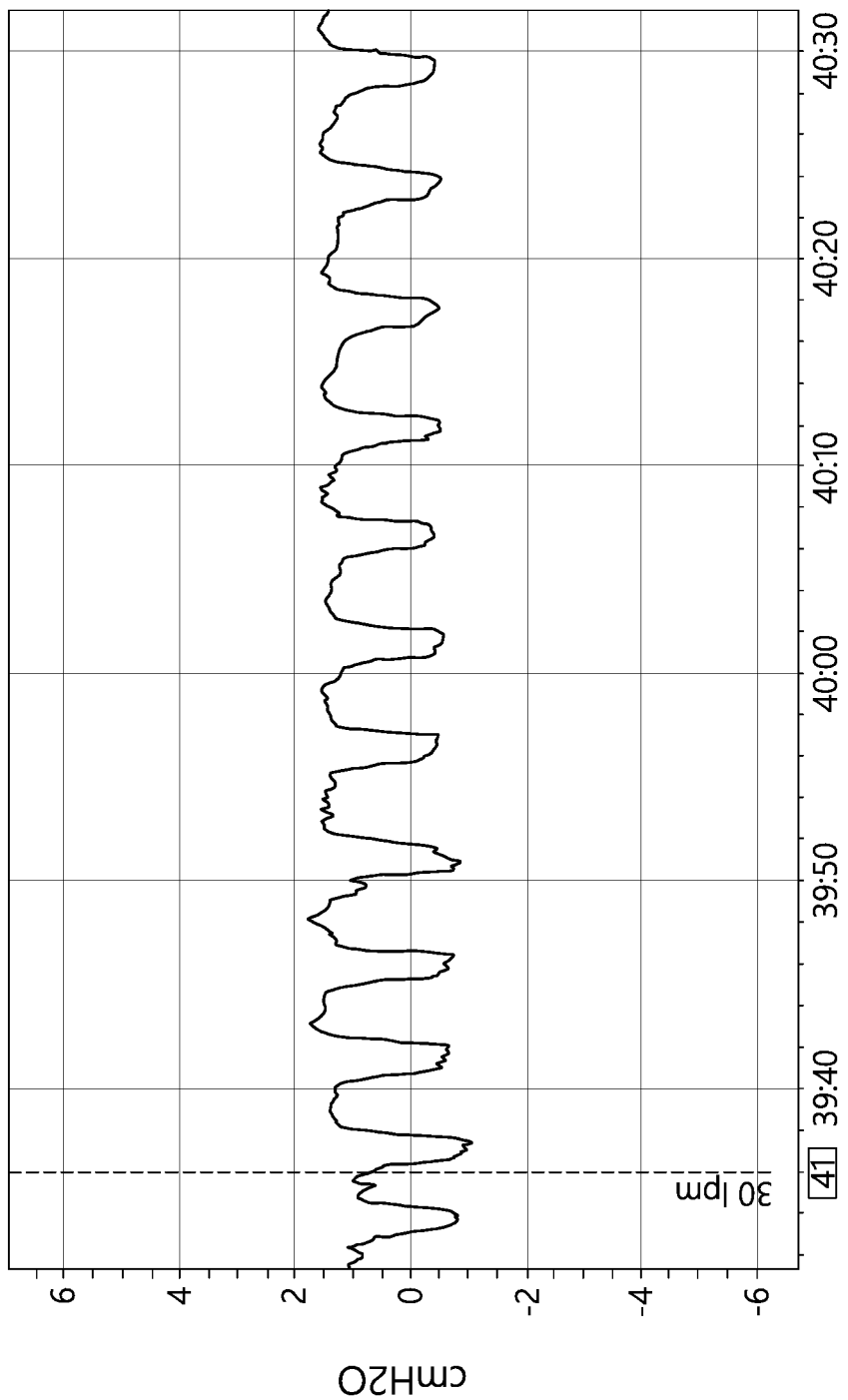
FIG. 6a is a graph of respiratory pressure with only a nasal cannula and without a mask.
Figure 6B:
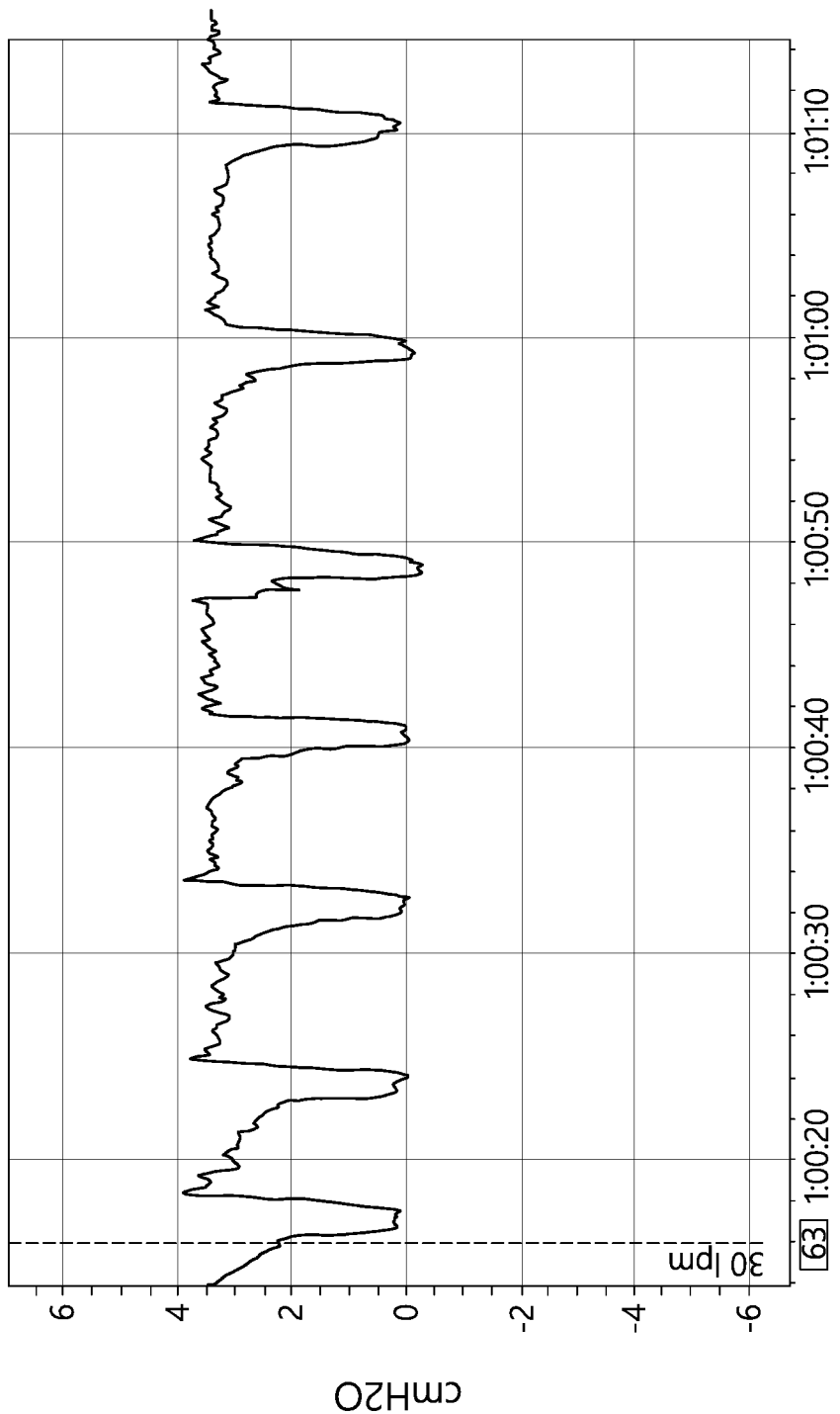
FIG. 6b is a graph of respiratory pressure with the combination of a nasal cannula and a mask.

FIGS. 6a and 6b demonstrate the impact that the application of the mask 100, 500 has when combined with a nasal cannula 102. FIG. 6a shows the pressure inside the nares of a patient when wearing a nasal cannula 102 supplying a flow rate of 30 L/min. FIG. 6b shows the pressure inside the nares of a patient wearing the mask 100, 500 in combination with a nasal cannula 102 supplying a flow rate of 30 L/min. It is apparent that the application of the mask 100, 500 over the top of a cannula 102 has the desired effects of increasing the respiration pressure, shown by the increased height of the wave form, and decreasing the respiration rate, as shown by the longer wavelength. It is shown that respiratory pressure is increased in both the inspiratory and expiratory phases of the user's breathing cycle. It is beneficial for the expiratory pressure to be increased as it can reduce respiratory distress, as shown by the decreased respiration rate.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to". Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The term "plurality" refers to two or more of an item. Any quantity, dimension, size, formulation, parameter, shape and other characteristic disclosed herein need not be exact, unless otherwise indicated, but can be interpreted as being preceded by the term "about" or "approximately." Accordingly, such quantity, dimension, size, formulation, parameter, shape and other characteristic can be approximated and/or larger or smaller, as desired, reflecting acceptable tolerances, conversion factors, rounding off, measurement error and the like and other factors known to those of skill in the art. Such terms can also be interpreted as being preceded by the term "substantially," which means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "1 to 3," "2 to 4" and "3 to 5," etc. This same principle applies to ranges reciting only one numerical value (e.g., "greater than 1") and should apply regardless of the breadth of the range or the characteristics being described.

A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

Reference to any prior art in this specification is not, and should not be taken as, an acknowledgement or any form of suggestion that that prior art forms part of the common general knowledge in the field of endeavour in any country in the world.

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. An interface system comprising:
   a nasal cannula comprising a cannula body, at least one nasal prong extending from the cannula body, a gases tube that communicates with the at least one nasal prong and a cannula retention arrangement that is coupled to the cannula body and configured to retain the nasal cannula on a head of a user;

a mask having a mask body, the mask body defining a user-contacting surface and an interior space when the user-contacting surface is in contact with a face of the user, the interior space of the mask being configured to accommodate at least a portion of the cannula body including the at least one nasal prong when the mask is positioned on the head of the user with the user-contacting surface in contact with the face of the user, the mask further comprising a one-way valve configured to open on inhalation and configured to at least partially close on exhalation;

the mask is adapted to create a seal around a nose and/or a mouth of the user when the mask is used in combination with the nasal cannula and is selectively securable to or removable from a user independently of the nasal cannula, the seal being sufficient to allow the interior space of the mask to be pressurized to provide increased respiratory pressure during inhalation and exhalation relative to use of the nasal cannula without the mask; and a variable vent configured to enable application of expiratory pressure to be selectively applied.

2. The interface system of claim 1, wherein the one-way valve remains open in an absence of inhalation by the user.

3. The interface system of claim 1, wherein the one-way valve is biased to a slightly open position.

4. The interface system of claim 3, wherein the one-way valve is biased such that 1-5 cm of gas pressure moves the one-way valve toward or to a closed position.

5. The interface system of claim 3, wherein the one-way valve is configured to move to a closed position from the slightly open position in response to an appropriate force.

6. The interface system of claim 1, wherein the variable vent is automatically controlled.

7. The interface system of claim 1, wherein the variable vent comprises an opening in the mask that allows a user to variably open and close the variable vent by blocking a portion or an entirety of the opening.

8. The interface system of claim 1, wherein the variable vent comprises a semicircular outlet that is partially or completely concealed by a vent cover.

9. The interface system of claim 8, wherein the vent cover is configured to move relative to the semicircular outlet or be removed from the semicircular outlet.

10. The interface system of claim 1, wherein the one-way valve is located on a lateral side of the mask; and/or the variable vent is centrally located on a front of the mask.

11. The interface system of claim 1, wherein the mask has a port that allows a Positive End Expiratory Pressure (PEEP) valve to be connected to the mask.

12. The interface system of claim 1, further comprising a vent that is or comprises a one-way drain valve that opens on inhalation to allow water accumulated in a region of the one-way drain valve to drain out during inhalation or opens on exhalation to allow water to be forced out of the mask.

13. The interface system of claim 1, further comprising a vent having an opening that is sealed with a manually removable plug or cap.

14. The interface system of claim 1, further comprising a condensation vent located on a downward facing surface of the mask body.

15. The interface system of claim 1, further comprising a fixed bias flow vent, the fixed bias flow vent comprising one or more small holes, a region of porous material, or a gap between a cushion and the nasal cannula or the face of the user.

16. The interface system of claim 15, wherein a geometry of the fixed bias flow vent is selected or configured to allow for a certain flow rate of air to pass through the fixed bias flow vent.

17. The interface system of claim 15, wherein the fixed bias flow vent comprises a series of small holes located in a central position on the mask.

18. The interface system of claim 1, wherein the mask does not include an air supply conduit or connection port.

19. The interface system of claim 1, wherein the mask body comprises a recess configured to accommodate, complement or match a lateral geometry of the nasal cannula to enable the nasal cannula to pass between the mask and the face of the user in use.

20. The interface system of claim 1, further comprising a vent that is or comprises a one-way drain valve configured to open on inhalation without reducing an internal pressure within the mask.

* * * * *